US009936864B2

(12) United States Patent
Tsutsui et al.

(10) Patent No.: US 9,936,864 B2
(45) Date of Patent: Apr. 10, 2018

(54) IMAGE PICKUP APPARATUS AND ELECTRONIC ENDOSCOPE SYSTEM

(71) Applicant: OLYMPUS CORPORATION, Tokyo (JP)

(72) Inventors: Keisuke Tsutsui, Saitama (JP); Fumiyuki Okawa, Tokyo (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 15/416,108

(22) Filed: Jan. 26, 2017

(65) Prior Publication Data

US 2017/0127924 A1 May 11, 2017

Related U.S. Application Data

(63) Continuation of application No. PCT/JP2016/054732, filed on Feb. 18, 2016.

(30) Foreign Application Priority Data

Jul. 13, 2015 (JP) .................................. 2015-139926

(51) Int. Cl.
| | |
|---|---|
| H04N 5/21 | (2006.01) |
| A61B 1/045 | (2006.01) |
| H04N 5/225 | (2006.01) |
| G02B 23/24 | (2006.01) |
| A61B 1/00 | (2006.01) |

(52) U.S. Cl.
CPC .......... *A61B 1/045* (2013.01); *A61B 1/00006* (2013.01); *A61B 1/00018* (2013.01); *G02B 23/2484* (2013.01); *H04N 5/2256* (2013.01); *H04N 2005/2255* (2013.01)

(58) Field of Classification Search
CPC .................................. H04N 5/21; H04N 7/18
USPC ..................................................... 348/65–77
See application file for complete search history.

(56) References Cited

U.S. PATENT DOCUMENTS

5,475,420 A * 12/1995 Buchin ................ A61B 1/0005
   348/65
2013/0176410 A1    7/2013  Takahashi et al.

FOREIGN PATENT DOCUMENTS

| CN | 103200859 A | 7/2013 |
| JP | 2011-206337 A | 10/2011 |
| WO | WO 2013/005719 A1 | 1/2013 |

* cited by examiner

*Primary Examiner* — Andy Rao
(74) *Attorney, Agent, or Firm* — Scully, Scott, Murphy & Presser, P.C.

(57) ABSTRACT

An image pickup apparatus includes a head portion including an image pickup device, and a connector portion integrally connected with the head portion via a cable. The head portion includes: an electronic shutter register configured to store a set value for controlling an image pickup device, among control data transmitted from the connector portion; and a communication circuit configured to, based on information indicating whether or not to transmit the set value for controlling the image pickup device, among the control data transmitted from the connector portion, to a register provided in the image pickup device, perform control of whether or not to transmit the set value stored in the electronic shutter register to the register provided in the image pickup device.

7 Claims, 10 Drawing Sheets

IMAGE PICKUP APPARATUS AND ELECTRONIC ENDOSCOPE SYSTEM

CROSS REFERENCE TO RELATED APPLICATION

This application is a continuation application of PCT/JP2016/054732 filed on Feb. 18, 2016 and claims benefit of Japanese Application No. 2015-139926 filed in Japan on Jul. 13, 2015, the entire contents of which are incorporated herein by this reference.

BACKGROUND OF THE INVENTION

1. Field of the Invention

The present invention relates to an image pickup apparatus and an electronic endoscope system which prevent an unintended value from being written to a register of an image pickup device and a register of a signal processing circuit controlled via a cable.

2. Description of the Related Art

Conventionally, an endoscope system provided with an endoscope is widely known in which the elongated endoscope is inserted into a body cavity or the like to perform observation of an examined site or various treatments. As such an endoscope system, for example, Japanese Patent Application Laid-Open Publication No. 2011-206337 discloses an endoscope system including an electronic endoscope provided with a solid-state image pickup device, and a processor apparatus connected to the electronic endoscope and configured to perform various signal processing for an image pickup signal from the solid-state image pickup device to convert the image pickup signal to image data. Then, the image data converted by the processor apparatus is displayed on a monitor connected via a cable to the processor apparatus.

Although a CCD solid-state image pickup device has been generally used as the solid-state image pickup device mounted on such an electronic endoscope conventionally, a CMOS solid-state image pickup device has also been used recently. The CMOS solid-state image pickup device is provided with registers for storing set values (control data) for driving and reading operations and the like, and the driving and reading operations are performed based on the control data set for the registers. The control data is transmitted from the processor apparatus to the electronic endoscope and set for the registers of the CMOS solid-state image pickup device.

By the way, surgical instruments such as an electrosurgical knife may be used during endoscope observation in the endoscope system, and it may happen that, during transmission of the control data or after the control data is stored in the registers, the control data is rewritten with unintended values by disturbance noise from the electrosurgical knife or the like. When rewriting of the control data due to disturbance noise or the like occurs as described above, an abnormality may occur in the driving and reading operations of the CMOS solid-state image pickup device.

Therefore, in the endoscope system of Japanese Patent Application Laid-Open Publication No. 2011-206337, the control data stored in the registers is superimposed on an image pickup signal outputted from the CMOS solid-state image pickup device to transmit the image pickup signal to the processor apparatus. Then, the endoscope system compares the control data superimposed on the image pickup signal and the control data set for the registers to detect whether rewriting of the control data stored in the registers has not occurred in the processor apparatus.

If detecting that rewriting of a set value has occurred, the endoscope system retransmits the control data from the processor apparatus to the CMOS solid-state image pickup device of the electronic endoscope. That is, if detecting an abnormality of control data stored in the registers, normal control data is transmitted to the registers of the CMOS solid-state image pickup device to reset the control data of registers so that the driving and reading operations of the CMOS solid-state image pickup device is returned to a normal state.

Thus, if the control data set for the registers of the CMOS solid-state image pickup device is rewritten with an abnormal value by influence of disturbance noise or the like, the driving and reading operations of the CMOS solid-state image pickup device can be returned to the normal state by resetting normal control data for the registers.

SUMMARY OF THE INVENTION

An image pickup apparatus of an aspect of the present invention is an image pickup apparatus including an image pickup portion including an image pickup device, and a controlling portion integrally connected with the image pickup portion via a cable, wherein the image pickup portion includes: a first register configured to store a set value for controlling the image pickup device among control data transmitted from the controlling portion; and a first communication circuit configured to, based on information indicating whether or not to transmit the set value for controlling the image pickup device, among the control data transmitted from the controlling portion, to a register provided in the image pickup device, perform control of whether or not to transmit the set value stored in the first register to the register provided in the image pickup device.

Further, an electronic endoscope system of an aspect of the present invention includes an image pickup portion including an image pickup device, and a controlling portion integrally connected with the image pickup portion via a cable; and the image pickup portion includes: a first register configured to store a set value for controlling the image pickup device among control data transmitted from the controlling portion; and a first communication circuit configured to, based on information indicating whether or not to transmit the set value for controlling the image pickup device, among the control data transmitted from the controlling portion, to a register provided in the image pickup device, perform control of whether or not to transmit the set value stored in the first register to the register provided in the image pickup device.

DETAILED DESCRIPTION OF THE PREFERRED EMBODIMENT(S)

Embodiments of the present invention will be described in detail below with reference to drawings.

First Embodiment

Figure 1:
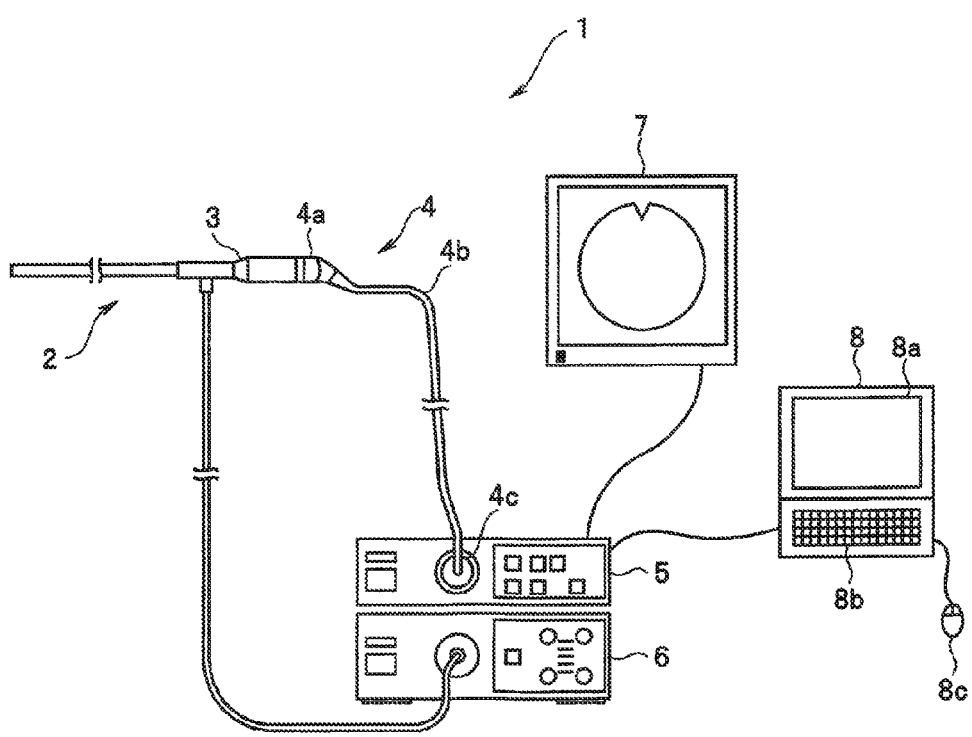
FIG. 1 is a diagram showing a configuration of an endoscope system according to a first embodiment.
Figure 2:
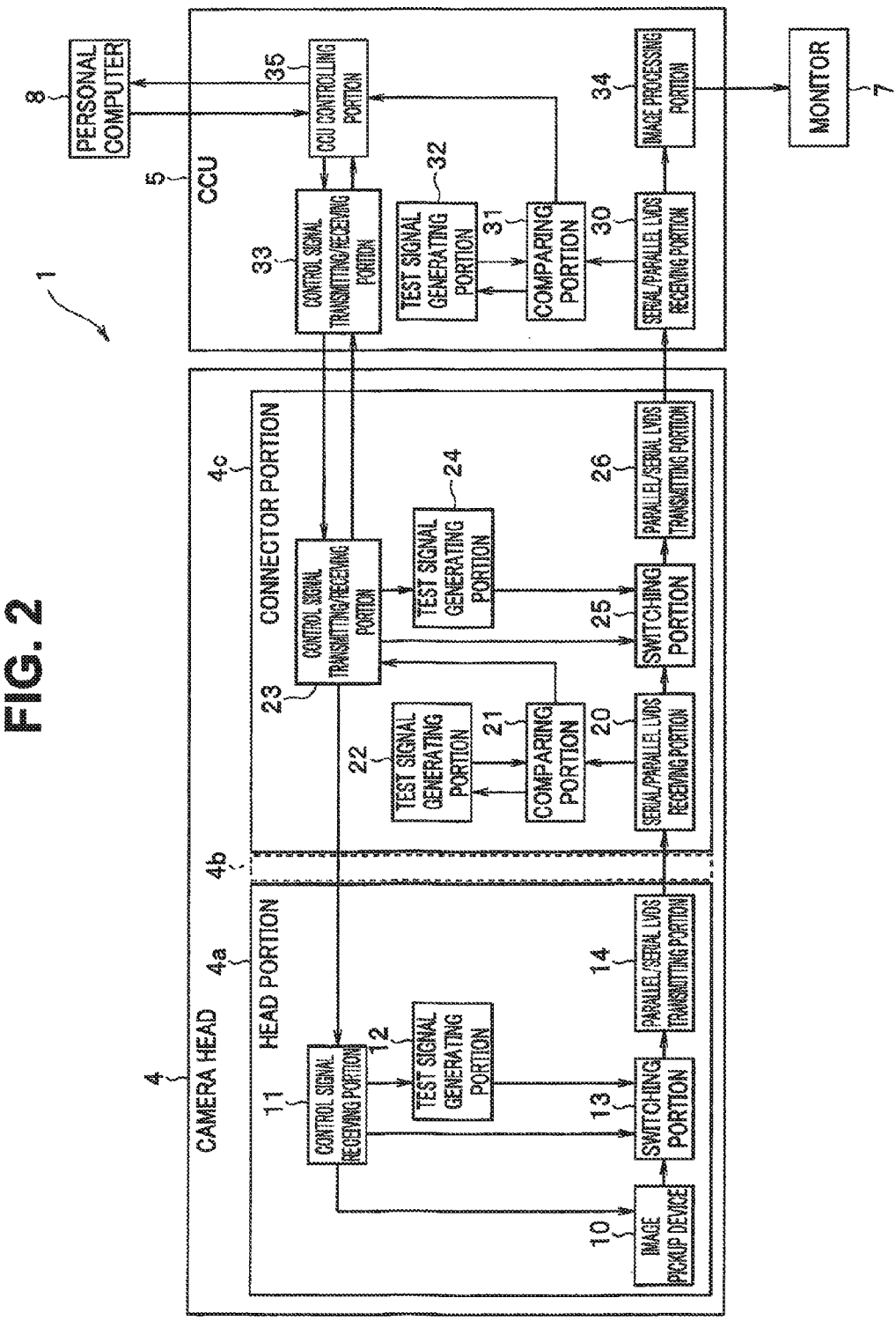
FIG. 2 is a diagram showing a detailed circuit configuration of a camera head and a camera control unit of the endoscope system according to the first embodiment.

FIG. 1 is a diagram showing a configuration of an endoscope system according to a first embodiment; and FIG. 2 is a diagram showing a detailed circuit configuration of a camera head and a camera control unit of the endoscope system according to the first embodiment.

As shown in FIG. 1, an endoscope system 1 is configured including, for example, an optical endoscope 2; a camera head 4 detachably connected to an eyepiece portion 3 of the endoscope 2; a camera control unit (hereinafter referred to as a CCU) 5 to which the camera head 4 is detachably connected; a light source apparatus 6 configured to supply illumination light to the endoscope 2; a monitor 7 configured to, by a video signal generated by an image processing portion of the CCU 5, which is to be described later, being inputted, display an observation image; and a personal computer 8 configured to give an instruction to start a comparison test to be described later, display a result of the comparison test, record the result of the comparison test, and the like.

The personal computer 8 includes a display portion 8a configured to display the result of the comparison test and the like, and a keyboard 8b and a mouse 8c for giving an instruction to start the comparison test and the like. Further, the personal computer 8 includes a recording portion not shown, which is configured to record the result of the comparison test.

The camera head 4 as an image pickup apparatus includes a head portion 4a to be connected to the eyepiece portion 3, a cable 4b extending from the head portion 4a and a connector portion 4c provided at a proximal end portion of the cable 4b. The camera head 4 is connected to the CCU 5 via the connector portion 4c.

Note that, though description will be made on assumption that the camera head 4 is connected to the endoscope 2, for example, other camera heads with different specifications for a magnification ratio and the like can be also connected. Further, an electronic endoscope can be also connected to the CCU 5.

As shown in FIG. 2, the head portion 4a is configured including an image pickup device 10 configured with a CMOS sensor, a control signal receiving portion 11, a test signal generating portion 12, a switching portion 13 and a parallel/serial LVDS transmitting portion 14. Note that the image pickup device 10 is not limited to a CMOS sensor but may be a CCD sensor or the like.

Further the connector portion 4c is configured including a serial/parallel LVDS receiving portion 20, a comparing portion 21, a test signal generating portion 22, a control signal transmitting/receiving portion 23, a test signal generating portion 24, a switching portion 25 and a parallel/serial LVDS transmitting portion 26.

Further, the CCU 5 is configured including a serial/parallel LVDS receiving portion 30, a comparing portion 31, a test signal generating portion 32, a control signal transmitting/receiving portion 33, an image processing portion 34 and a CCU controlling portion 35.

Illumination light from the light source apparatus 6 is transmitted to the endoscope 2 via a light guide not shown and illuminated to an object from a distal end face of an insertion portion via the light guide not shown inside the insertion portion. Return light from the object is image-picked up by the image pickup device 10 of the head portion 4a. An image pickup signal which has been image-picked up by the image pickup device 10 is outputted to the switching portion 13.

During normal endoscope observation, the switching portion 13 outputs the image pickup signal from the image pickup device 10 to the parallel/serial LVDS transmitting portion 14 of the connector portion 4c. Note that, in a case of performing a comparison test to be described later, the switching portion 13 outputs a test signal generated by the test signal generating portion 12 to the parallel/serial LVDS transmitting portion 14 based on a switching signal from the control signal receiving portion 11.

The parallel/serial LVDS transmitting portion 14 converts the inputted image pickup signal from parallel to serial and transmits the image pickup signal to the serial/parallel LVDS receiving portion 20 as an LVDS (low-voltage differential signal). The serial/parallel LVDS receiving portion 20 converts the received image pickup signal from serial to parallel and outputs the image pickup signal to the switching portion 25.

During the normal endoscope observation, the switching portion 25 outputs the image pickup signal from the serial/parallel LVDS receiving portion 20 to the parallel/serial LVDS transmitting portion 26. Note that, in the case of performing the comparison test to be described later, the switching portion 25 outputs a test signal generated by the test signal generating portion 24 to the parallel/serial LVDS transmitting portion 26 based on a switching signal from the control signal transmitting/receiving portion 23.

The parallel/serial LVDS transmitting portion 26 converts the inputted image pickup signal from parallel to serial and transmits the image pickup signal to the serial/parallel LVDS receiving portion 30 as an LVDS. The serial/parallel LVDS receiving portion 30 converts the received image pickup signal from serial to parallel and outputs the image pickup signal to the image processing portion 34.

The image processing portion 34 performs predetermined image processing for the inputted image signal to generate a video signal, and outputs the generated video signal to the monitor 7 to display an observation image on the monitor 7.

Here, description will be made on an example of a procedure for a comparison test of data transmission between the head portion 4a and the connector portion 4c.

First, a user operates the keyboard 8b or the mouse 8c of the personal computer 8 to transmit a command giving an instruction to start a comparison test, from the personal computer 8 to the CCU controlling portion 35. The CCU controlling portion 35 transmits the command transmitted from the personal computer 8, to the control signal transmitting/receiving portion 33. The control signal transmitting/receiving portion 33 transmits the command transmitted from the CCU controlling portion 35, to the control signal transmitting/receiving portion 23 of the connector portion 4c, and the control signal transmitting/receiving portion 23 transmits the command transmitted from the control signal transmitting/receiving portion 33, to the control signal receiving portion 11 of the head portion 4a.

When receiving the command giving an instruction to start a comparison test, the control signal receiving portion 11 of the head portion 4a transmits a test signal generation starting signal to the test signal generating portion 12 as well as transmitting a switching signal for switching to a test signal transmission mode, to the switching portion 13. When the test signal generation starting signal is inputted, the test signal generating portion 12 generates a test signal for performing a bit error rate test and outputs the test signal to the switching portion 13.

When the switching signal is inputted from the control signal receiving portion 11, the switching portion 13 outputs the test signal generated by the test signal generating portion 12 to the parallel/serial LVDS transmitting portion 14. The parallel/serial LVDS transmitting portion 14 as a first transmitting portion converts the test signal inputted from the switching portion 13 from parallel to serial, and transmits the test signal to the serial/parallel LVDS receiving portion 20 of the connector portion 4c as an LVDS.

The serial/parallel LVDS receiving portion 20 as a first receiving portion receives the test signal from the parallel/serial LVDS transmitting portion 14, converts the test signal from serial to parallel and outputs the test signal to the comparing portion 21. When detecting a predetermined data pattern from the inputted test signal, the comparing portion 21 outputs a generation starting signal for starting generation of a test signal, to the test signal generating portion 22. When the generation starting signal is inputted, the test signal generating portion 22 generates a test signal which is a same pattern signal as the test signal generated by the test signal generating portion 12 and outputs the generated test signal to the comparing portion 21.

The comparing portion 21 compares the test signal from the serial/parallel LVDS receiving portion 20 and the test signal from the test signal generating portion 22 and outputs a comparison result to the control signal transmitting/receiving portion 23. If the comparison result indicates correspondence, that is, if the test signal from the serial/parallel LVDS receiving portion 20 and the test signal from the test signal generating portion 22 correspond to each other, it is judged that there is not an error in the data transmission between the head portion 4a and the connector portion 4c. On the other hand, if the comparison result indicates non-correspondence, that is, if the test signal from the serial/parallel LVDS receiving portion 20 and the test signal from the test signal generating portion 22 do not correspond to each other, it is judged that there is an error in the data transmission between the head portion 4a and the connector portion 4c.

The control signal transmitting/receiving portion 23 transmits the comparison result from the comparing portion 21, to the control signal transmitting/receiving portion 33 of the CCU 5. The control signal transmitting/receiving portion 33 transmits the received comparison result to the CCU controlling portion 35. The personal computer 8 acquires the comparison result by accessing the CCU controlling portion 35; and then displays the acquired comparison result on the display portion 8a and records the acquired comparison result to a recording portion such as a memory.

Next, description will be made on an example of a procedure for a comparison test of data transmission between the connector portion 4c and the CCU 5.

First, the user operates the keyboard 8b or the mouse 8c of the personal computer 8 to transmit a command giving an instruction to start a comparison text, from the personal computer 8 to the CCU controlling portion 35. The CCU controlling portion 35 transmits the command transmitted from the personal computer 8, to the control signal transmitting/receiving portion 33, and the control signal transmitting/receiving portion 33 transmits the command transmitted from the CCU controlling portion 35, to the control signal transmitting/receiving portion 23 of the connector portion 4c.

When receiving the command giving an instruction to start a comparison test, the control signal transmitting/receiving portion 23 of the connector portion 4c transmits a test signal generation starting signal to the test signal generating portion 24 as well as transmitting a switching signal for switching to a test signal transmission mode, to the switching portion 25. When the test signal generation starting signal is inputted, the test signal generating portion 24 generates a test signal for performing a bit error rate test and outputs the test signal to the switching portion 25.

When the switching signal is inputted from the control signal transmitting/receiving portion 23, the switching portion 25 outputs the test signal generated by the test signal generating portion 24 to the parallel/serial LVDS transmitting portion 26. The parallel/serial LVDS transmitting portion 26 as a second transmitting portion converts the test signal inputted from the switching portion 25 from parallel to serial, and transmits the test signal to the serial/parallel LVDS receiving portion 30 of the CCU 5 as an LVDS.

The serial/parallel LVDS receiving portion 30 as a second receiving portion receives the test signal from the parallel/serial LVDS transmitting portion 26, converts the test signal from serial to parallel and outputs the test signal to the comparing portion 31. When detecting a predetermined data pattern from the inputted test signal, the comparing portion 31 outputs a generation starting signal for starting generation of a test signal, to the test signal generating portion 32. When the generation starting signal is inputted, the test signal generating portion 32 generates a test signal which is a same pattern signal as the test signal generated by the test signal generating portion 24 and outputs the generated test signal to the comparing portion 31.

The comparing portion 31 compares the test signal from the serial/parallel LVDS receiving portion 30 and the test signal from the test signal generating portion 32 and outputs a comparison result to the CCU controlling portion 35. A judgment method is similar to the judgment method at the time of the data transmission between the head portion 4a and the connector portion 4c described above. It is judged that there is not an error in the data transmission between the connector portion 4c and the CCU 5 if a comparison result indicates correspondence, and it is judged that there is an error in the data transmission between the connector portion 4c and the CCU 5 if the comparison result indicates non-correspondence.

The personal computer 8 acquires the comparison result by accessing the CCU controlling portion 35; and then displays the acquired comparison result on the display portion 8a and stores the acquired comparison result to a storing portion such as a memory.

Note that the command giving an instruction to perform a comparison test of data transmission between the head portion 4a and the connector portion 4c and a command giving an instruction to perform a comparison test of data transmission between the connector portion 4c and the CCU 5 may be a same command or may be different commands, respectively. That is, it is possible to perform two comparison tests with one command, and it is also possible to perform the comparison test of data transmission between the head portion 4a and the connector portion 4c and the comparison test of data transmission between the connector portion 4c and the CCU 5 with a first command and a second command, respectively.

Next, a process for setting control data which is set for the image pickup device 10 and the test signal generating portion 12 will be described.

Control data set for the test signal generating portion 12 as a signal processing circuit configured to perform signal processing in the image pickup device 10 and the head portion 4a is transmitted from the CCU controlling portion 35 of the CCU 5. The CCU controlling portion 35 transmits the control data to the control signal transmitting/receiving portion 23 of the connector portion 4c via the control signal transmitting/receiving portion 33. The control signal transmitting/receiving portion 23 transmits the control data to the control signal receiving portion 11 of the head portion 4a via the cable 4b.

The control signal receiving portion 11 judges whether or not to transmit the control data to the image pickup device 10 and the test signal generating portion 12. Then, if judging that transmission is possible, the control signal receiving portion 11 transmits the control data to the image pickup device 10 and the test signal generating portion 12, and performs setting of the control data for each of registers of the image pickup device 10 and the test signal generating portion 12.

Figure 3:
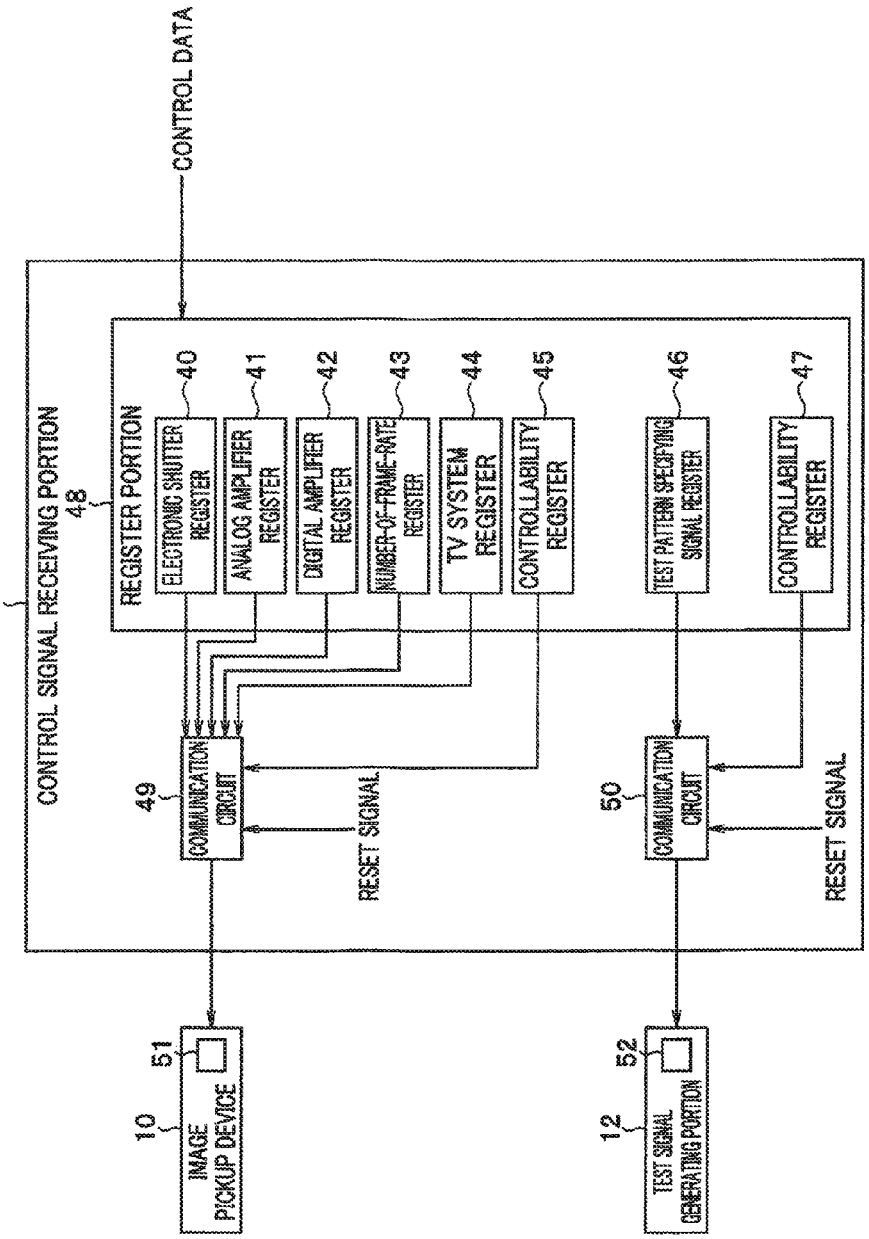
FIG. 3 is a diagram for illustrating a detailed circuit configuration of a control signal receiving portion according to a first embodiment.

Description will be made on a detailed circuit configuration of the control signal receiving portion 11 configured to perform such setting of the control data using FIG. 3. FIG. 3 is a diagram for illustrating the detailed circuit configuration of the control signal receiving portion according to the first embodiment.

As shown in FIG. 3, the control signal receiving portion 11 is configured including a register portion 48 including an electronic shutter register 40, an analog amplifier register 41, a digital amplifier register 42, a number-of-frame-rate register 43, a TV system register 44, a controllability register 45, a test pattern specifying signal register 46 and a controllability register 47; and a communication circuits 49 and 50.

The control data transmitted from the CCU controlling portion 35 is inputted to the register portion 48. A set value (a register value) for performing control of an electronic shutter of the image pickup device 10, among the inputted control data, is stored into the electronic shutter register 40. Further, a set value (a register value) for an analog amplifier of the image pickup device 10, among the inputted control data, is stored into the analog amplifier register 41. Further, a set value (a register value) for a digital amplifier of the image pickup device 10, among the inputted control data, is stored into the digital amplifier register 42. Further, a set value (a register value) for a number of frame rate (for example, 60 fps and 30 fps) of the image pickup device 10, among the inputted control data, is stored into the number-of-frame-rate register 43. Further, a set value (a register value) for a reading cycle (for example, 60 Hz and 50 Hz) of the image pickup device 10, among the inputted control data, is stored into the TV system register 44. The electronic shutter register 40, the analog amplifier register 41, the digital amplifier register 42, the number-of-frame-rate register 43 and the TV system register 44 constitute a first register.

Further, information (a register value) for judging whether or not to transmit the set values of the electronic shutter register 40, the analog amplifier register 41, the digital amplifier register 42, the number-of-frame-rate register 43 and the TV system register 44, among the inputted control data, to the image pickup device 10 is stored into the controllability register 45 which constitutes a second register.

Further, a set value (a register value) for specifying a pattern of a test signal to be generated by the test signal generating portion 12, among the inputted control data, is stored into the test pattern specifying signal register 46 which constitutes a third register. Further, information (a register value) for judging whether or not to transmit the set value of the test pattern specifying signal register 46, among the inputted control data, to the test signal generating portion 12 is stored into the controllability register 47 which constitutes a fourth register.

The communication circuit 49 which constitutes a first communication circuit performs control of whether or not to transmit the set values of the electronic shutter register 40, the analog amplifier register 41, the digital amplifier register 42, the number-of-frame-rate register 43 and the TV system register 44 to a register 51 of the image pickup device 10 according to the information (the register value) of the controllability register 45.

More specifically, if the register value of the controllability register 45 is, for example, "A5A" of 12 bits, the communication circuit 49 performs control to transmit the set value of the electronic shutter register 40 to the register 51 of the image pickup device 10. On the other hand, if the register value of the controllability register 45 is, for example, a value other than "A5A", the communication circuit 49 performs control not to transmit the set value of the electronic shutter register 40 to the register 51 of the image pickup device 10. The image pickup device 10 performs control of the electronic shutter according to the set value set for the register 51.

Note that the controllability register 45 may be configured to have a plurality of 12-bit register values. For example, if the controllability register 45 includes three registers, and each of the three registers of the controllability register 45 becomes "A5A", the communication circuit 49 performs control to transmit the set value of the electronic shutter register 40 to the register 51 of the image pickup device 10. On the other hand, if each of the three register values of the controllability register 45 is a value other than "A5A", the communication circuit 49 performs control not to transmit the set value of the electronic shutter register 40 to the register 51 of the image pickup device 10. Thereby, an effect of decreasing probability of an error occurring in the controllability register 45 itself can be expected.

Further, though the control of whether or not to transmit the set values of the electronic shutter register 40, the analog amplifier register 41, the digital amplifier register 42, the number-of-frame-rate register 43 and the TV system register 44 to the register 51 of the image pickup device 10 is performed based on the information (the register value) of the controllability register 45 in the present embodiment, this is not limiting. For example, it is also possible to provide the controllability register 45 for each of the electronic shutter register 40, the analog amplifier register 41, the digital amplifier register 42, the number-of-frame-rate register 43 and the TV system register 44 individually, and perform control of whether or not to transmit each set value to the register 51 of the image pickup device 10 individually.

Further, it is also possible to provide the controllability register 45 only for the number-of-frame-rate register 43 in which the number of fields to be read out, which depends on an operation mode, is stored, without providing the controllability register 45 for the electronic shutter register 40 where set values which are continuously used, such as the set value of the electronic shutter, are stored.

Furthermore, though the control of whether or not to transmit each set value to the register 51 of the image pickup device 10 is performed based on the information of the controllability register 45, it is also possible to input a reset signal such as an H/L level signal to the communication circuit 49 and control whether or not to transmit each set value to the register 51 of the image pickup device 10 based on the reset signal as shown in FIG. 3.

Note that the set values set for the register 51 of the image pickup device 10 are not limited to the set value for controlling the electronic shutter, but set values for performing various processes of the image pickup device 10 are included.

Further, the communication circuit 50 which constitutes a second communication circuit performs control of whether or not to transmit the set value of the test pattern specifying signal register 46 to a register 52 of the test signal generating portion 12 according to the information (the register value) of the controllability register 47.

More specifically, if the register value of the controllability register 47 is, for example, "A5A" of 12 bits, the communication circuit 50 performs control to transmit the set value of the test pattern specifying signal register 46 to the register 52 of the test signal generating portion 12. On the other hand, if the register value of the controllability register 47 is, for example, a value other than "A5A", the communication circuit 50 performs control not to transmit the set value of the test pattern specifying signal register 46 to the register 52 of the test signal generating portion 12. The test signal generating portion 12 generates a test signal of a pattern corresponding to the set value set for the register 52.

Note that the controllability register 47 may be configured to have a plurality of 12-bit register values. For example, if the controllability register 47 includes three registers, and each of the three registers of the controllability register 47 becomes "A5A", the communication circuit 50 performs control to transmit the set value of the test pattern specifying signal register 46 to the register 52 of the test signal generating portion 12. On the other hand, if each of the three register values of the controllability register 47 is a value other than "A5A", the communication circuit 50 performs control not to transmit the set value of the test pattern specifying signal register 46 to the register 52 of the test signal generating portion 12. Thereby, an effect of decreasing probability of an error occurring in the controllability register 47 itself can be expected.

Note that the set value set for the register 52 of the test signal generating portion 12 is not limited to a set value for specifying the pattern of a test signal, but set values for performing various processes of the test signal generating portion 12 are included.

As described above, the endoscope system 1 is provided with the controllability registers 45 and 47, and controls whether or not to transmit a set value for controlling each processing portion to the image pickup device 10 and the test signal generating portion 12 by the communication circuits 49 and 50 according to the register values of the controllability registers 45 and 47.

When control data is transmitted from the CCU 5 to the control signal receiving portion 11 of the head portion 4a, a register value indicating that transmission is possible is set for the controllability registers 45 and 47, and, therefore, set values of the electronic shutter register 40 and the test pattern specifying signal register 46 are set for the register 51 of the image pickup device 10 and the register 52 of the test signal generating portion 12, respectively.

On the other hand, when disturbance noise or the like is applied to the cable 4b and inputted to the control signal receiving portion 11, a value other than a register value indicating that control is possible is set for the controllability registers 45 and 47. Therefore, it does not happen that an unintended value such as disturbance noise is set for the register 51 of the image pickup device 10 and the register 52 of the test signal generating portion 12. As a result, the endoscope system 1 can prevent an unintended value such as disturbance noise is written to the register 51 of the image pickup device 10 and the register 52 of the test signal generating portion 12.

Further, the control signal receiving portion 11 may be adapted to transmit respective register values set for the respective registers 40 to 47 to the switching portion 13. The switching portion 13 may be configured to superimpose the register values from the control signal receiving portion 11 during a blanking period of an image pickup signal from the image pickup device 10 to transmit the register values to the connector portion 4c. The connector portion 4c may compare a register value transmitted to the head portion 4a by the control signal transmitting/receiving portion 23 and a register value received from the head portion 4a to judge whether or not to retransmit a register value according to a comparison result. Further, when, even if the connector portion 4c retransmits a register value to the head portion 4a for a predetermined period, the register value does not correspond to a register value received from the head portion 4a, the connector portion 4c may transmit a reset signal to the head portion 4a.

Therefore, according to the endoscope system of the present embodiment, it is possible to prevent unintended control data from being written to a register of the image pickup device.

First Modification of First Embodiment

Next, a first modification of the first embodiment will be described.

Figure 4:
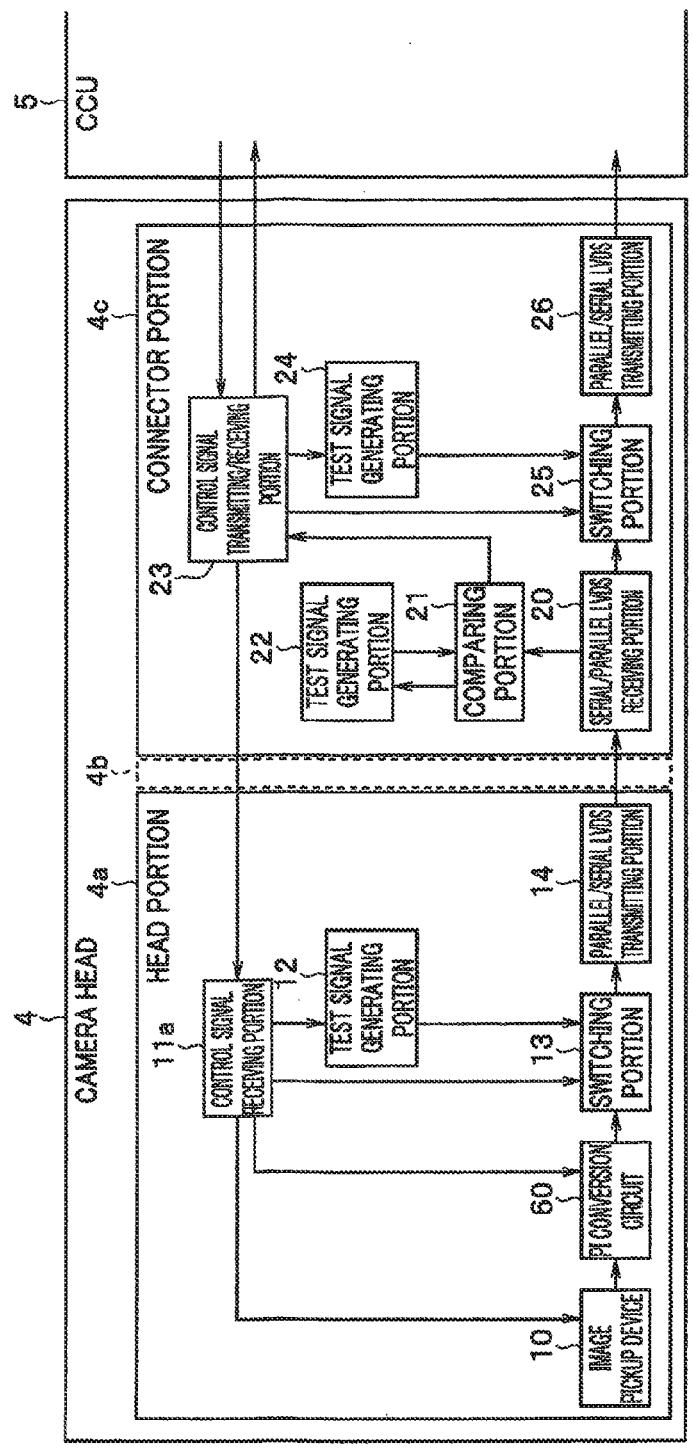
FIG. 4 is a diagram for illustrating a detailed circuit configuration of a camera head according to a first modification of the first embodiment.

FIG. 4 is a diagram for illustrating a detailed circuit configuration of a camera head according to the first modification of the first embodiment. Note that, in FIG. 4, components similar to the components of FIG. 2 will be given same reference numerals, and description of the components will be omitted.

As shown in FIG. 4, the head portion 4a of the first modification of the first embodiment is configured by adding a progressive/interlace (hereinafter referred to as PI) conversion circuit 60 to the head portion 4a of FIG. 2, between the image pickup device 10 and the switching portion 13. Further, the head portion 4a is configured with a control signal receiving portion 11a instead of the control signal receiving portion 11 of the head portion 4a of FIG. 2.

In a case where the image pickup device 10 is a progressive scan type image pickup device, and the monitor 7 is an NTSC type or PAL type monitor, the PI conversion circuit 60 as a signal processing circuit configured to perform signal processing in the head portion 4a converts a progressive image pickup signal inputted from the image pickup device 10 to an interlace image pickup signal to cause the image pickup signal to be compatible with a TV type of the monitor 7 and outputs the image pickup signal to the switching portion 13. More specifically, the PI conversion circuit 60 averages two vertical-direction lines of one frame from the image pickup device 10, converts a result to an odd/even field and outputs the odd/even field to the switching portion 13. That is, the PI conversion circuit 60 averages first and second lines of one frame to generate a first line of an odd field, averages the second and third lines to generate a first line of an even field.

The control signal receiving portion 11a performs control for mode setting and the like for the PI conversion circuit 60. At this time, it is controlled whether or not to transmit a set value to the PI conversion circuit 60 based on information of a controllability register as described below.

Figure 5:
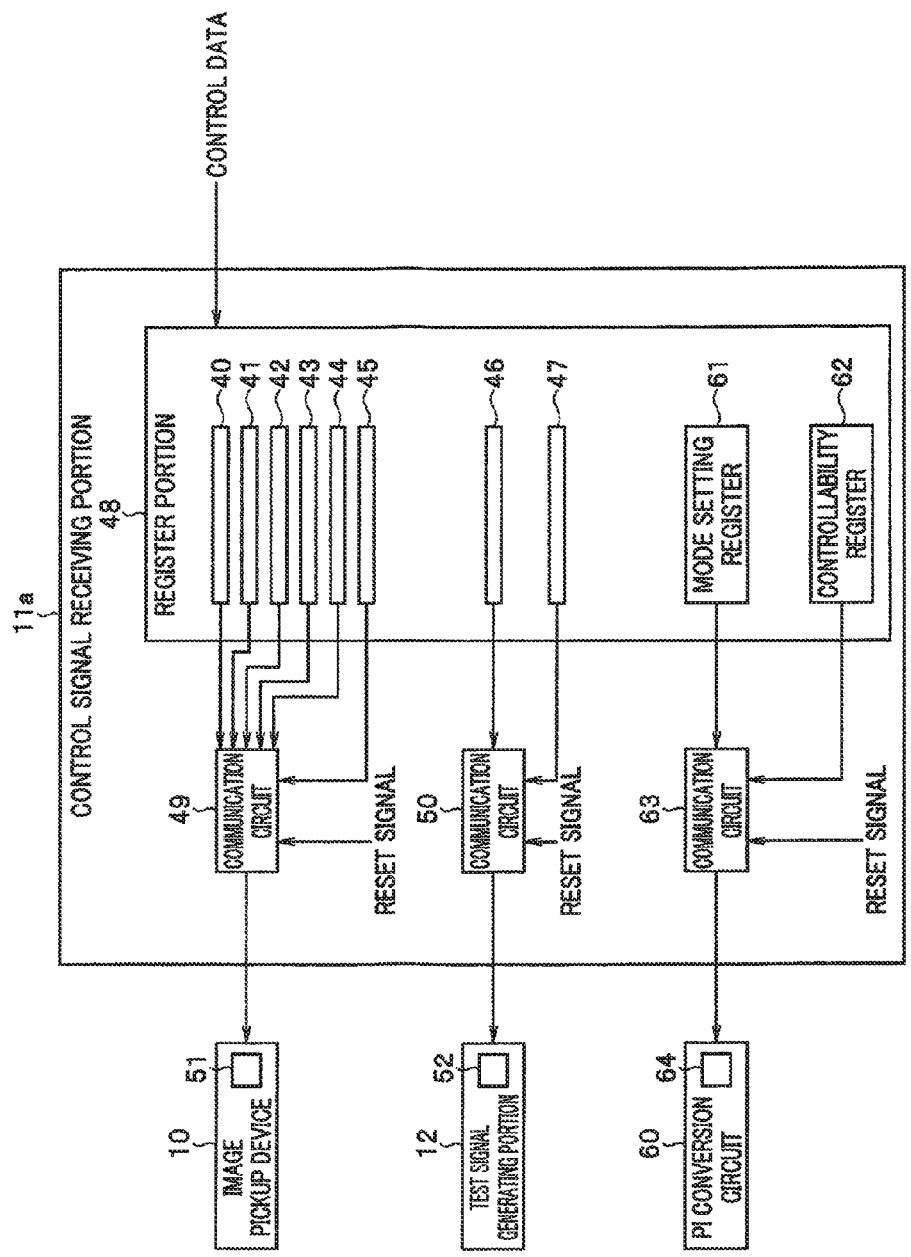
FIG. 5 is a diagram for illustrating a detailed circuit configuration of a control signal receiving portion according to the first modification of the first embodiment.

FIG. 5 is a diagram for illustrating a detailed circuit configuration of the control signal receiving portion according to the first modification of the first embodiment. Note that, in FIG. 5, components similar to the components of FIG. 3 will be given same reference numerals, and description of the components will be omitted. As shown in FIG. 5, the control signal receiving portion 11a is configured by adding a mode setting register 61, a controllability register 62 and a communication circuit 63 to the control signal receiving portion 11 of FIG. 3.

In the mode setting register 61 which constitutes a third register, a set value (a register value) for performing setting of a mode for the PI conversion circuit 60, among inputted control data, is stored. Further, in the controllability register 62 which constitutes a fourth register, information (a register value) for judging whether or not to transmit the set value of the mode setting register 61, among the inputted control data, to the PI conversion circuit 60 is stored.

The communication circuit 63 which constitutes a second communication circuit performs control of whether or not to transmit the set value of the mode setting register 61 to a register 64 of the PI conversion circuit 60 according to the information (the register value) of the controllability register 62. Note that the communication circuit 63 may control whether or not to transmit the set value of the mode setting register 61 to the register 64 of the PI conversion circuit 60 according to a reset signal such as an H/L level signal.

Due to the above configuration, according to the endoscope system of the first modification of the first embodiment, it is possible to perform control of the image pickup device 10 in the head portion 4a and control of a signal processing circuit (here, the test signal generating portion 12 and the PI conversion circuit 60) in the head portion 4a.

Second Modification of First Embodiment

Next, a second modification of the first embodiment will be described.

Figure 6:
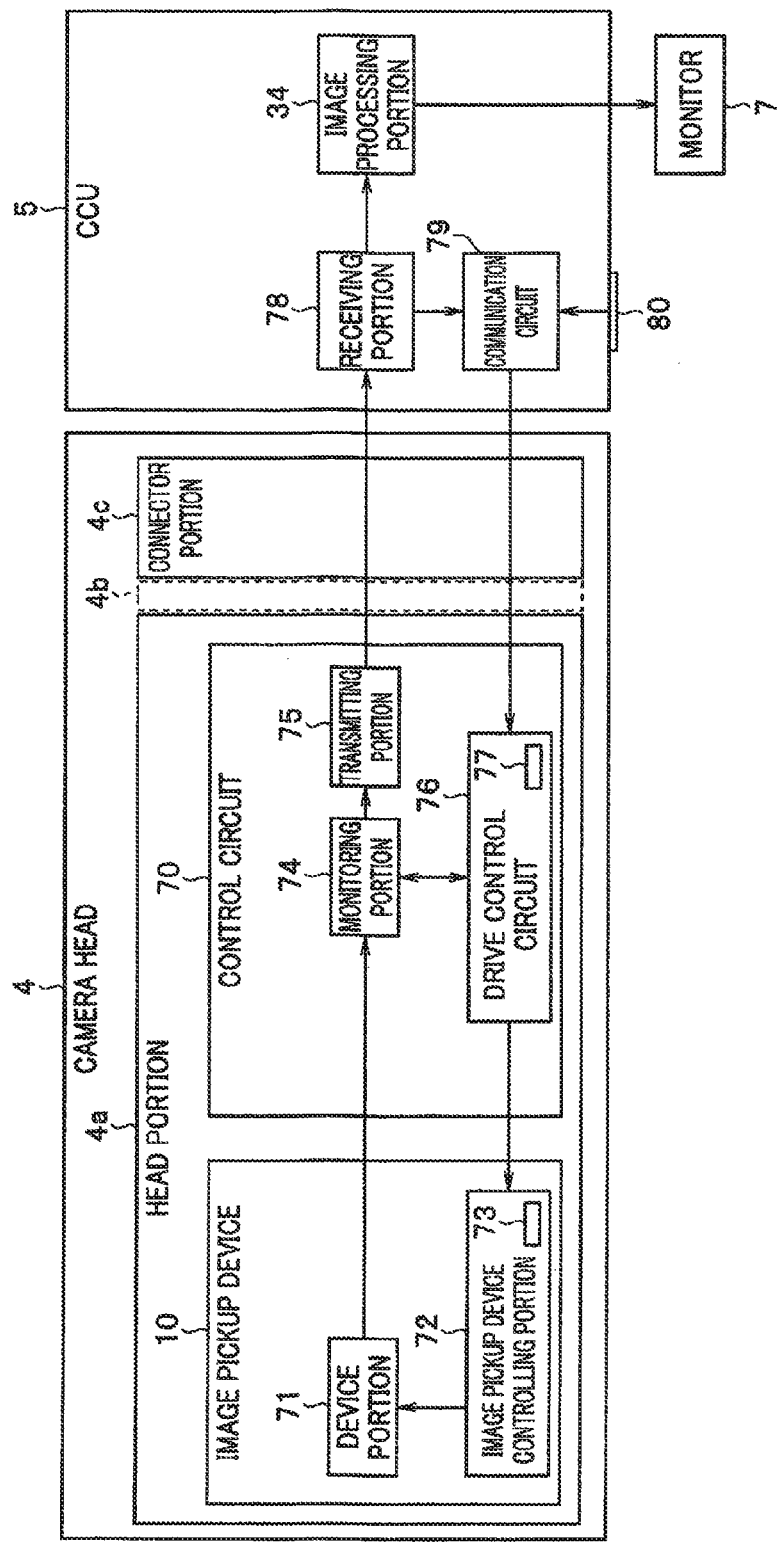
FIG. 6 is a diagram showing a detailed circuit configuration of a camera head and a camera control unit according to a second modification of the first embodiment.

FIG. 6 is a diagram showing a detailed circuit configuration of a camera head and a camera control unit according to the second modification of the first embodiment. Note that, in FIG. 6, components similar to the components of FIG. 2 will be given same reference numerals, and description of the components will be omitted.

As shown in FIG. 6, the head portion 4a is configured including, in addition to the image pickup device 10, a control circuit 70 configured to monitor a read signal from the image pickup device 10 and, when the read signal from the image pickup device 10 is abnormal, perform initialization of the image pickup device 10 again.

The image pickup device 10 is configured including a device portion 71 and an image pickup device controlling portion 72 configured to control the device portion 71. The image pickup device controlling portion 72 is provided with a register 73 configured to hold a set value for controlling the device portion 71.

Further, the control circuit 70 is configured including a monitoring portion 74, a transmitting portion 75 and a drive control circuit 76. The drive control circuit 76 is provided with a register portion 77 configured to hold set values to be set for the register 73 of the image pickup device controlling portion 72 and for the monitoring portion 74.

Further, the CCU 5 is configured including a receiving portion 78, a communication circuit 79 and an operation portion 80 in addition to the image processing portion 34. The CCU 5 can rewrite (change) a set value set for the register portion 77 via the operation portion 80.

When the user operates the operation portion 80 to give an instruction to rewrite the set value, the communication circuit 79 performs communication with the drive control circuit 76. Then, the communication circuit 79 transmits a set value newly set to the drive control circuit 76 to rewrite the set value of the register portion 77. Similarly to the first embodiment, the drive control circuit 76 performs control of whether or not to transmit the set value of the register portion 77 to the image pickup device controlling portion 72 and the monitoring portion 74 according to information of a controllability register.

Further, an image pickup signal which is image-picked up by the device portion 71 of the image pickup device 10 is outputted to the monitoring portion 74. The monitoring portion 74 as a signal processing circuit configured to perform signal processing in the head portion 4a outputs the image pickup signal from the device portion 71 to the transmitting portion 75 and monitors whether the image pickup signal is not abnormal. Further, if detecting that the image pickup signal is abnormal, the monitoring portion 74 outputs an initialization starting signal to the drive control circuit 76. When the initialization starting signal is inputted from the monitoring portion 74, the drive control circuit 76 performs initialization of the image pickup device 10 again.

The transmitting portion 75 converts the inputted image signal from parallel to serial and transmits the image pickup signal to the receiving portion 78 of the CCU 5 as an LVDS. The receiving portion 78 converts the received image pickup signal from serial to parallel and outputs the image pickup signal to the image processing portion 34. The image processing portion 34 performs predetermined image processing for the inputted image signal to generate a video signal, and outputs the generated video signal to the monitor 7 to display an observation image on the monitor 7.

Figure 7:
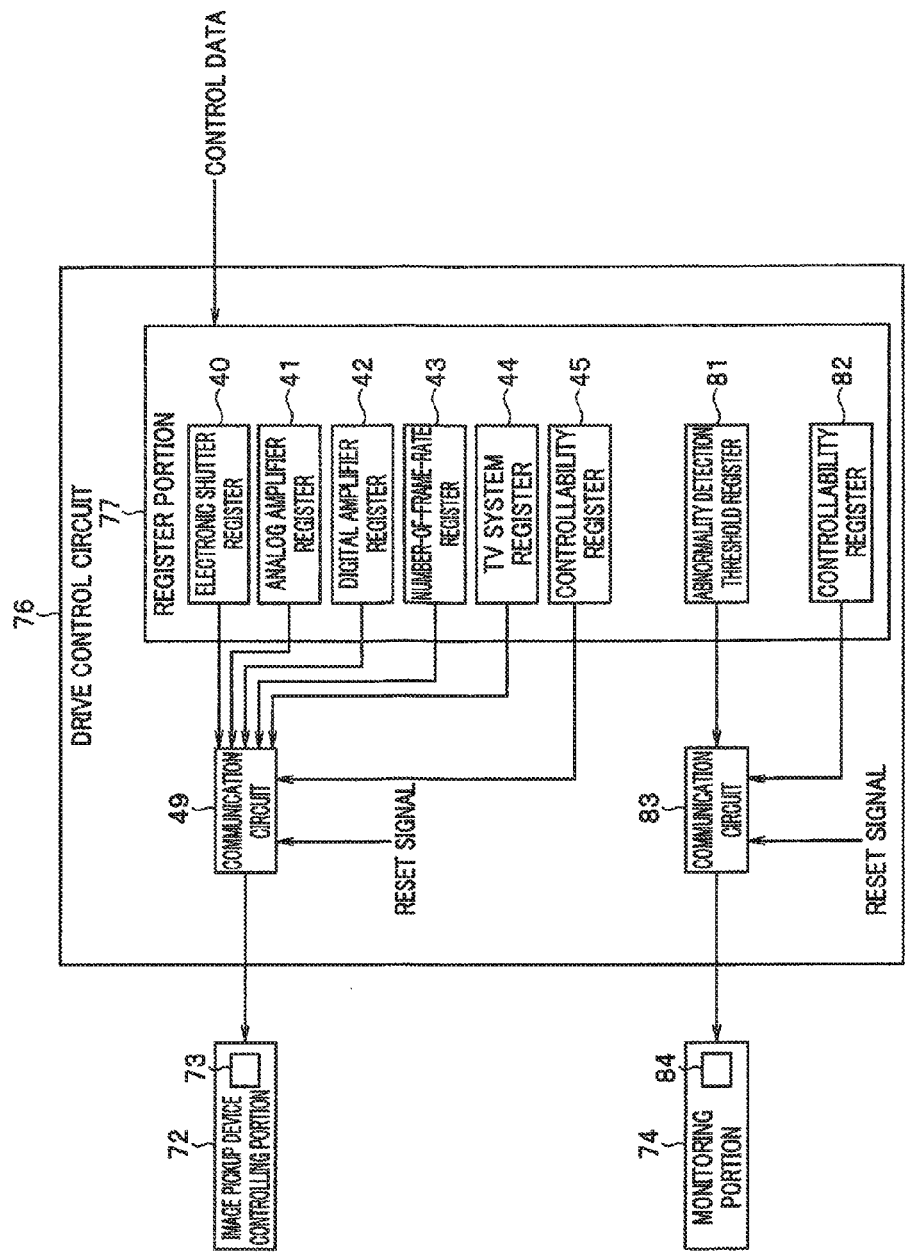
FIG. 7 is a diagram for illustrating a detailed circuit configuration of a drive control circuit 76.

FIG. 7 is a diagram for illustrating a detailed circuit configuration of the drive control circuit 76. Note that, in FIG. 7, components similar to the components of FIG. 3 will be given same reference numerals, and description of the components will be omitted.

As shown in FIG. 7, the register portion 77 of the drive control circuit 76 is configured being provided with, in addition to the electronic shutter register 40, the analog amplifier register 41, the digital amplifier register 42, the number-of-frame-rate register 43, the TV system register 44 and the controllability register 45, an abnormality detection threshold register 81 and a controllability register 82. Further, the drive control circuit 76 is configured including a communication circuit 83 in addition to the communication circuit 49.

In the abnormality detection threshold register 81 which constitutes a third register, a threshold for detecting an abnormality of an image pickup signal by the monitoring portion 74 is stored. Further, in the controllability register 82 which constitutes a fourth register, information (a register value) for judging whether or not to transmit a set value of the abnormality detection threshold register 81, among inputted control data, to the monitoring portion 74 is stored.

Similarly to the first embodiment, the communication circuit 49 performs control of whether or not to transmit a set value of each of the registers 40 to 44 to the register 73 of the image pickup device controlling portion 72 according to information (a register value) of the controllability register 45. The image pickup device controlling portion 72 performs various processes of the image pickup device 10 according to set values set for the register 73.

Further, the communication circuit 83 which constitutes a second communication circuit performs control of whether or not to transmit a set value of the abnormality detection threshold register 81 to a register 84 of the monitoring portion 74 according to information (a register value) of the controllability register 82. The monitoring portion 74 executes detection of an abnormality of an image signal according to a set value (threshold) set for the register 84.

Due to the above configuration, according to the endoscope system of the second modification of the first embodiment, it is possible to perform control of the image pickup device 10 in the head portion 4*a* and control of a signal processing circuit (here, the monitoring portion 74) in the head portion 4*a*. Note that the endoscope system of the second modification of the first embodiment may perform control of other signal processing circuits (the test signal generating portion 12 and the PI conversion circuit 60 described above) in addition to control of the image pickup device 10 and the monitoring portion 74 though it is not shown.

Second Embodiment

In the first embodiment, description has been made on the endoscope system 1 capable of preventing an unintended signal such as disturbance noise applied to the cable 4*b* from being written to the register 51 of the image pickup device 10 and the register 52 of the test signal generating portion 12. However, there may be a case where set values of the register 51 of the image pickup device 10 and the register 52 of the test signal generating portion 12 are directly rewritten by disturbance noise or the like. Therefore, in a second embodiment, description will be made on the endoscope system 1 capable of resetting normal setting values when the set values of the register 51 of the image pickup device 10 and the register 52 of the test signal generating portion 12 are rewritten with unintended values.

Figure 8:
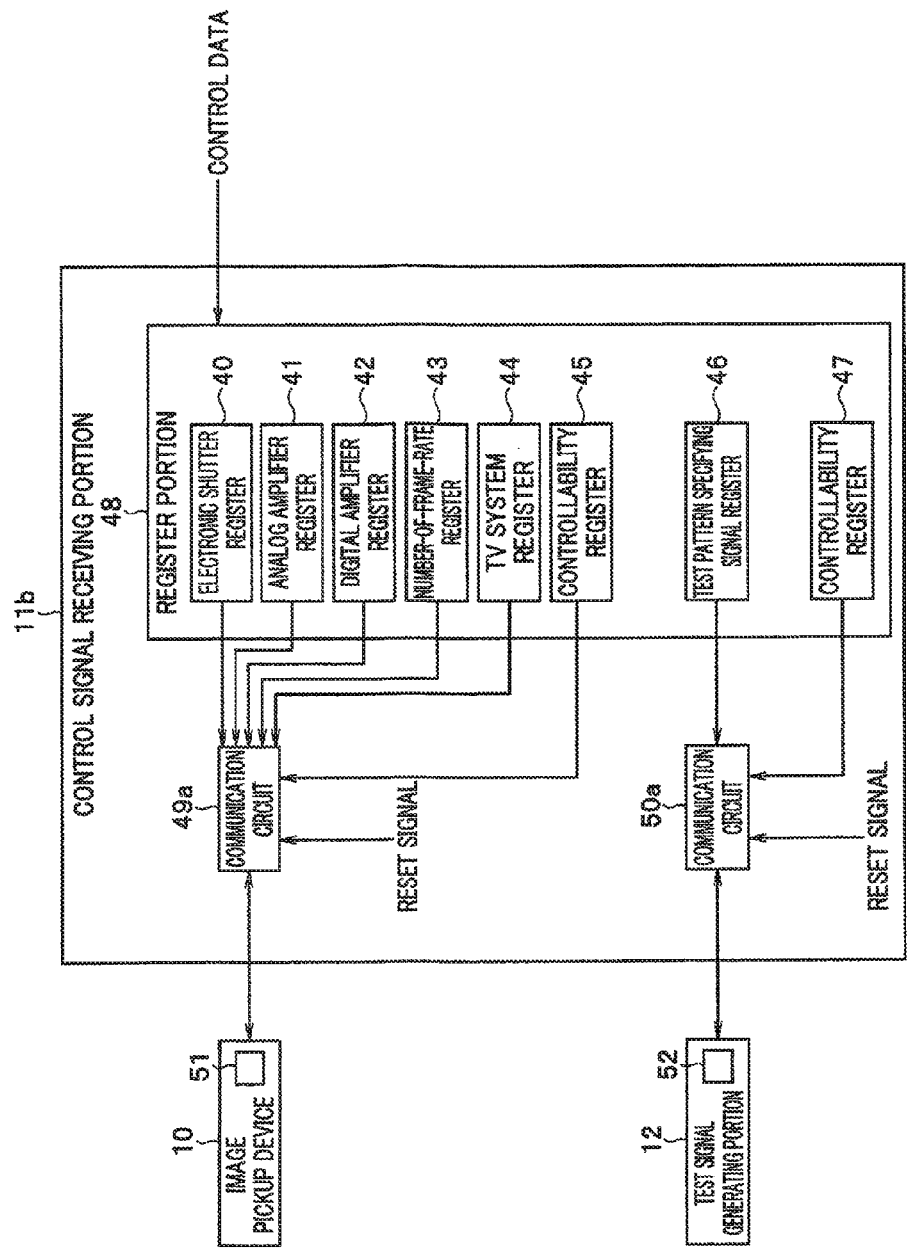
FIG. 8 is a diagram for illustrating a detailed circuit configuration of a control signal receiving portion according to a second embodiment.

FIG. 8 is a diagram for illustrating a detailed circuit configuration of a control signal receiving portion according to the second embodiment. Note that, in FIG. 8, components similar to the components of FIG. 3 will be given same reference numerals, and description of the components will be omitted. As shown in FIG. 8, a control signal receiving portion 11*b* is configured with communication circuits 49*a* and 50*a* instead of the communication circuits 49 and 50 of the control signal receiving portion 11 of FIG. 3, respectively.

The communication circuit 49*a* reads set values of the register 51 of the image pickup device 10 and compares the set values with respective set values of the electronic shutter register 40, the analog amplifier register 41, the digital amplifier register 42, the number-of-frame-rate register 43 and the TV system register 44. Then, if the set values of the register 51 of the image pickup device 10 do not correspond to the respective set values of the electronic shutter register 40, the analog amplifier register 41, the digital amplifier register 42, the number-of-frame-rate register 43 and the TV system register 44, the communication circuit 49*a* performs control to set the respective set values of the electronic shutter register 40, the analog amplifier register 41, the digital amplifier register 42, the number-of-frame-rate register 43 and the TV system register 44 to the register 51 of the image pickup device 10 again. Note that the communication circuit 49*a* may set only set values that do not correspond to the set values of the register 51 of the image pickup device 10 again.

Note that the control signal receiving portion 11*b* may be configured to include a reset circuit for resetting the image pickup device 10. When the set values of the register 51 of the image pickup device 10 do not correspond to the respective set values of the electronic shutter register 40, the analog amplifier register 41, the digital amplifier register 42, the number-of-frame-rate register 43 and the TV system register 44 even if the communication circuit 49*a* resets the respective set values of the electronic shutter register 40, the analog amplifier register 41, the digital amplifier register 42, the number-of-frame-rate register 43 and the TV system register 44 to the register 51 of the image pickup device 10 a predetermined number of times, the reset circuit resets the image pickup device 10.

Further, the communication circuit 50*a* reads a set value of the register 52 of the test signal generating portion 12 and compares the set value with a set value of the test pattern specifying signal register 46. Then, if the set value of the register 52 of the test signal generating portion 12 does not correspond to the set value of the test pattern specifying signal register 46, the communication circuit 50*a* performs control to set the set value of the test pattern specifying signal register 46 to the register 52 of the test signal generating portion 12 again.

Note that, the reset circuit described above may reset the test signal generating portion 12. That is, when, even if the communication circuit 50*a* resets the set value of the test pattern specifying signal register 46 for the register 52 of the test signal generating portion 12 a predetermined number of times, the set value of the register 52 of the test signal generating portion 12 does not correspond to the set value of the test pattern specifying signal register 46, the reset circuit resets the test signal generating portion 12.

Thereby, even if a set value of the register 51 of the image pickup device 10 and a set value of the register 52 of the test signal generating portion 12 are rewritten with unintended values by disturbance noise caused by an electrosurgical knife or the like, the endoscope system 1 of the second embodiment can immediately reset normal set values stored in the electronic shutter register 40 and the test pattern specifying signal register 46 for the register 51 of the image pickup device 10 and the register 52 of the test signal generating portion 12.

Modification of Second Embodiment

Next, a modification of the second embodiment will be described.

Figure 9:
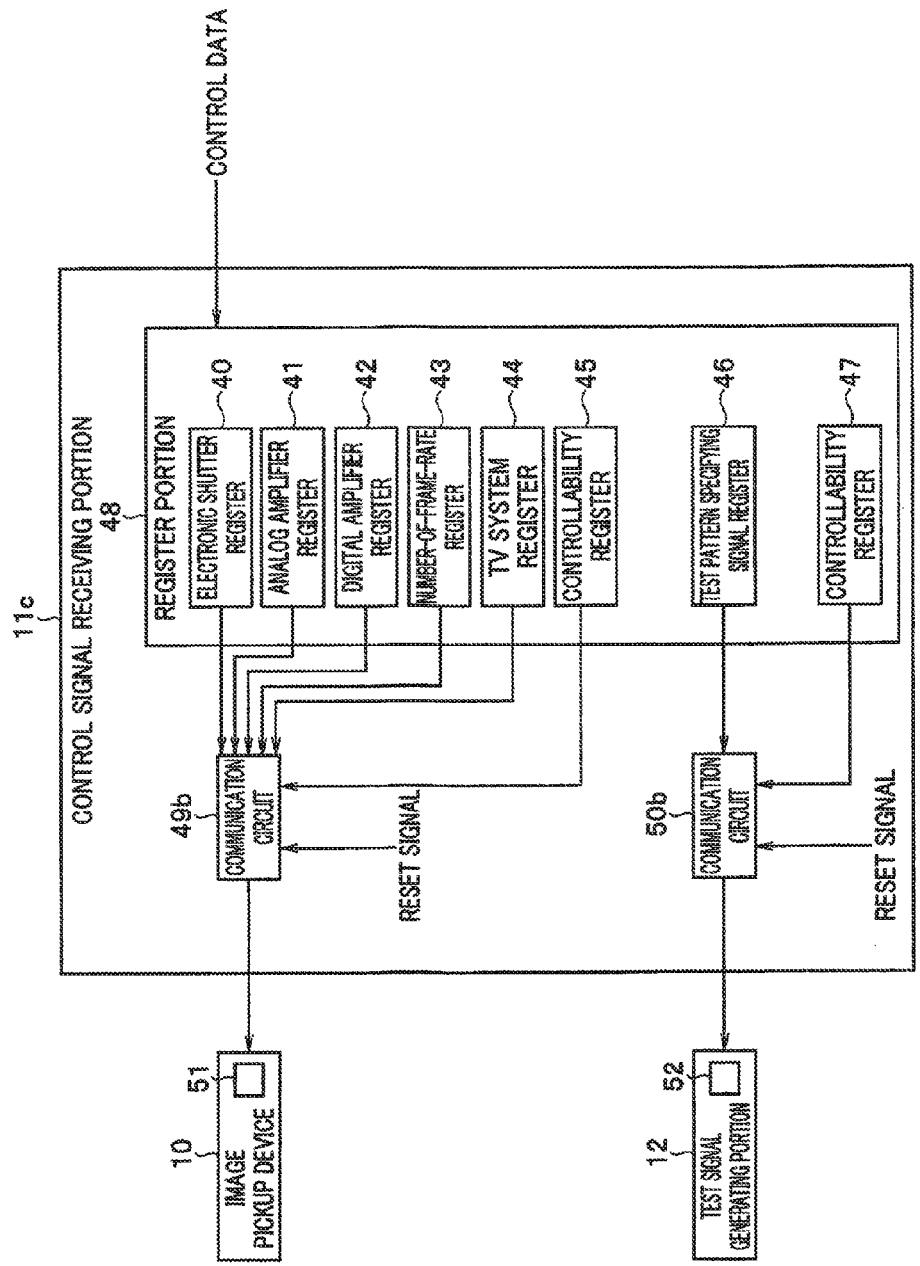
FIG. 9 is a diagram for illustrating a detailed circuit configuration of a control signal receiving portion according to a modification of the second embodiment.

FIG. 9 is a diagram for illustrating a detailed circuit configuration of a control signal receiving portion according to the modification of the second embodiment. Note that, in FIG. 9, components similar to the components of FIG. 4 will be given same reference numerals, and description of the components will be omitted. As shown in FIG. 9, a control signal receiving portion 11c is configured with communication circuits 49b and 50b instead of the communication circuits 49a and 50a of the control signal receiving portion 11b of FIG. 8, respectively.

The communication circuit 49b periodically writes a set value of the electronic shutter register 40 to the register 51 of the image pickup device 10. Further, the communication circuit 50b periodically writes a set value of the test pattern specifying signal register 46 to the register 52 of the test signal generating portion 12. Other components are similar to the components of the second embodiment.

Thereby, even if a set value of the register 51 of the image pickup device 10 and a set value of the register 52 of the test signal generating portion 12 are rewritten with unintended values by disturbance noise caused by an electrosurgical knife or the like, the endoscope system 1 of the modification can immediately reset normal set values for the register 51 of the image pickup device 10 and the register 52 of the test signal generating portion 12 similarly to the second embodiment.

Third Embodiment

Next, a third embodiment will be described.

Figure 10:
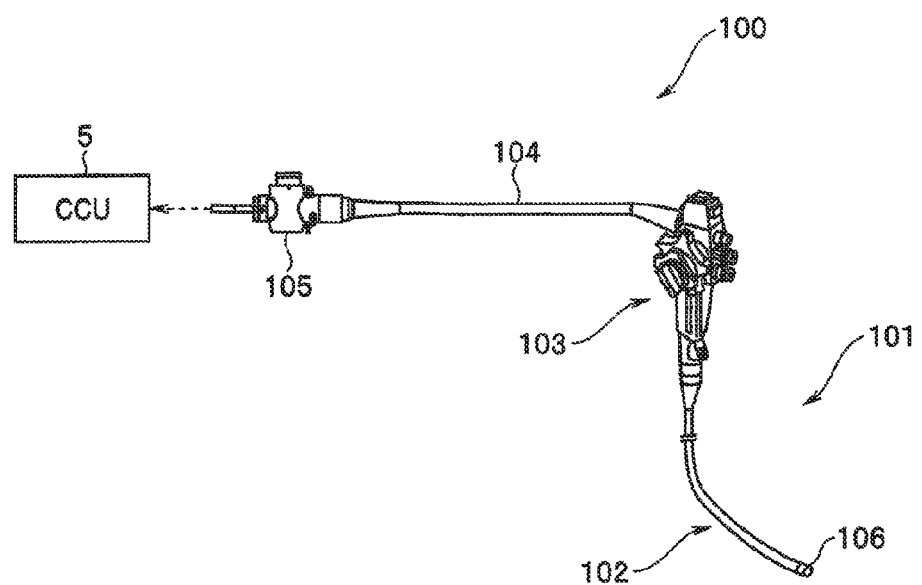
FIG. 10 is a diagram showing a configuration of an electronic endoscope system according to a third embodiment.

FIG. 10 is a diagram showing a configuration of an electronic endoscope system according to the third embodiment. As shown in FIG. 10, an electronic endoscope system 100 is provided with an endoscope 101 and the CCU 5 detachably connected to the endoscope 101.

The endoscope 101 is configured, for example, as an electronic endoscope, and is provided with a long insertion portion with a small diameter configured to be inserted into a subject, an operation portion 103 provided being connected to a proximal end side of the insertion portion 102, a cable 104 extended in a lateral direction from a proximal end side of the operation portion 103 and a connector portion 105 provided at a proximal end portion of the cable 104. The endoscope 101 is configured to be detachably connected to the CCU 5 via the connector portion 105. A distal end portion 106 is provided at a distal end of the insertion portion 102.

The connector portion 105 is provided with respective circuits such as the control signal transmitting/receiving portion 23 similarly to the connector portion 4c of FIG. 2. Further, the distal end portion 106 is provided with respective circuits such as the image pickup device 10, the control signal receiving portion 11 and the test signal generating portion 12 similarly to the head portion 4a of FIG. 2.

Control data from the CCU 5 is transmitted to the distal end portion 106 from the connector portion 105 via the cable 104. Then, the distal end portion 106 controls about whether or not to set the transmitted control data for the image pickup device 10 according to a register value of a controllability register. As a result, according to the endoscope system of the present embodiment, it is possible to prevent unintended control data from being written to a resistor of the image pickup device, similarly to the first embodiment.

The present invention is not limited to the embodiments described above, but various changes, alterations and the like are possible within a range not departing from the spirit of the present invention.

What is claimed is:

1. An image pickup apparatus comprising:
   an image sensor configured to capture an image of an object;
   a controller connected with the image sensor;
   a first register configured to store a first set value for controlling the image sensor among control data transmitted from the controller; and
   a first communication circuit configured to perform control of whether or not to transmit the first set value stored in the first register to a second register provided in the image sensor based on control information transmitted from the controller.

2. The image pickup apparatus according to claim 1, further comprising a third register configured to store the control information.

3. The image pickup apparatus according to claim 1, further comprising:
   a signal processing circuit configured to perform signal processing in the image pickup apparatus;
   a fourth register configured to store a second set value for controlling the signal processing circuit among the control data transmitted from the controller;
   a fifth register configured to store another control information indicating whether or not to transmit the second set value to a sixth register provided in the signal processing circuit; and
   a second communication circuit configured to perform control of whether or not to transmit the second set value stored in the fourth register to the sixth register provided in the signal processing circuit based on the another control information stored in the fifth register.

4. The image pickup apparatus according to claim 3, wherein
   the first communication circuit reads another first set value set for the second register of the image sensor, compares the another first set value with the first set value stored in the first register, and if the another first set value set for the second register of the image sensor does not correspond to the first set value stored in the first register, the first communication circuit resets the first set value stored in the first register; and
   the second communication circuit reads another second set value set for the sixth register of the signal processing circuit, compares the another second set value with the second set value stored in the fourth register, and if the another second set value set for the sixth register of the signal processing circuit does not correspond to the second set value stored in the fourth register, the second communication circuit resets the second set value stored in the fourth register.

5. The image pickup apparatus according to claim 1, wherein the first communication circuit periodically writes the first set value stored in the first register to the second register of the image sensor.

6. The image pickup apparatus according to claim 3, wherein the second communication circuit periodically writes the second set value stored in the fourth register to the sixth register of the signal processing circuit.

7. An electronic endoscope system comprising the image pickup apparatus according to claim 1.

* * * * *